(12) United States Patent
Jaryal et al.

(10) Patent No.: US 8,604,208 B2
(45) Date of Patent: Dec. 10, 2013

(54) POLYMORPHS OF SORAFENIB ACID ADDITION SALTS

(75) Inventors: Jagdev Singh Jaryal, Kangra (IN); Swargam Sathyanarayana, Karim Nagar (IN); Rajesh Kumar Thaper, Jammu (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/497,861

(22) PCT Filed: Sep. 24, 2010

(86) PCT No.: PCT/IB2010/054324
§ 371 (c)(1),
(2), (4) Date: May 9, 2012

(87) PCT Pub. No.: WO2011/036648
PCT Pub. Date: Mar. 31, 2011

(65) Prior Publication Data
US 2012/0264789 A1    Oct. 18, 2012

(30) Foreign Application Priority Data

Sep. 24, 2009 (IN) .......................... 2008/DEL/2009

(51) Int. Cl.
*A61K 31/44* (2006.01)
*C07D 213/81* (2006.01)

(52) U.S. Cl.
USPC ........................................ 546/268.1; 514/350

(58) Field of Classification Search
None
See application file for complete search history.

(56) References Cited

FOREIGN PATENT DOCUMENTS

| CN | 101 584 661 | 11/2009 |
|---|---|---|
| WO | WO 00/42012 | 7/2000 |
| WO | WO 2006/034796 | 4/2006 |
| WO | WO 2006/034797 | 4/2006 |
| WO | WO 2008/113177 | 9/2008 |
| WO | WO 2009/034308 | 3/2009 |
| WO | WO 2009/054004 | 4/2009 |
| WO | WO 2009/092070 | 7/2009 |
| WO | WO 2009/106825 | 9/2009 |
| WO | WO 2010/142678 | 12/2010 |

OTHER PUBLICATIONS

Caira, M.R., "Crystalline Polymorphism of Organic Compounds", *Topics in Current Chemistry*, Edited by E. Weber et al., 198:163-208 (1998).

*Primary Examiner* — Janet Andres
*Assistant Examiner* — Heidi Reese

(57) ABSTRACT

The present invention provides amorphous and crystalline forms of acid addition salts of sorafenib, pharmaceutical compositions comprising them and their use for the treatment of cancer. The present invention also provides processes for the preparation of acid addition salts of sorafenib.

5 Claims, 19 Drawing Sheets

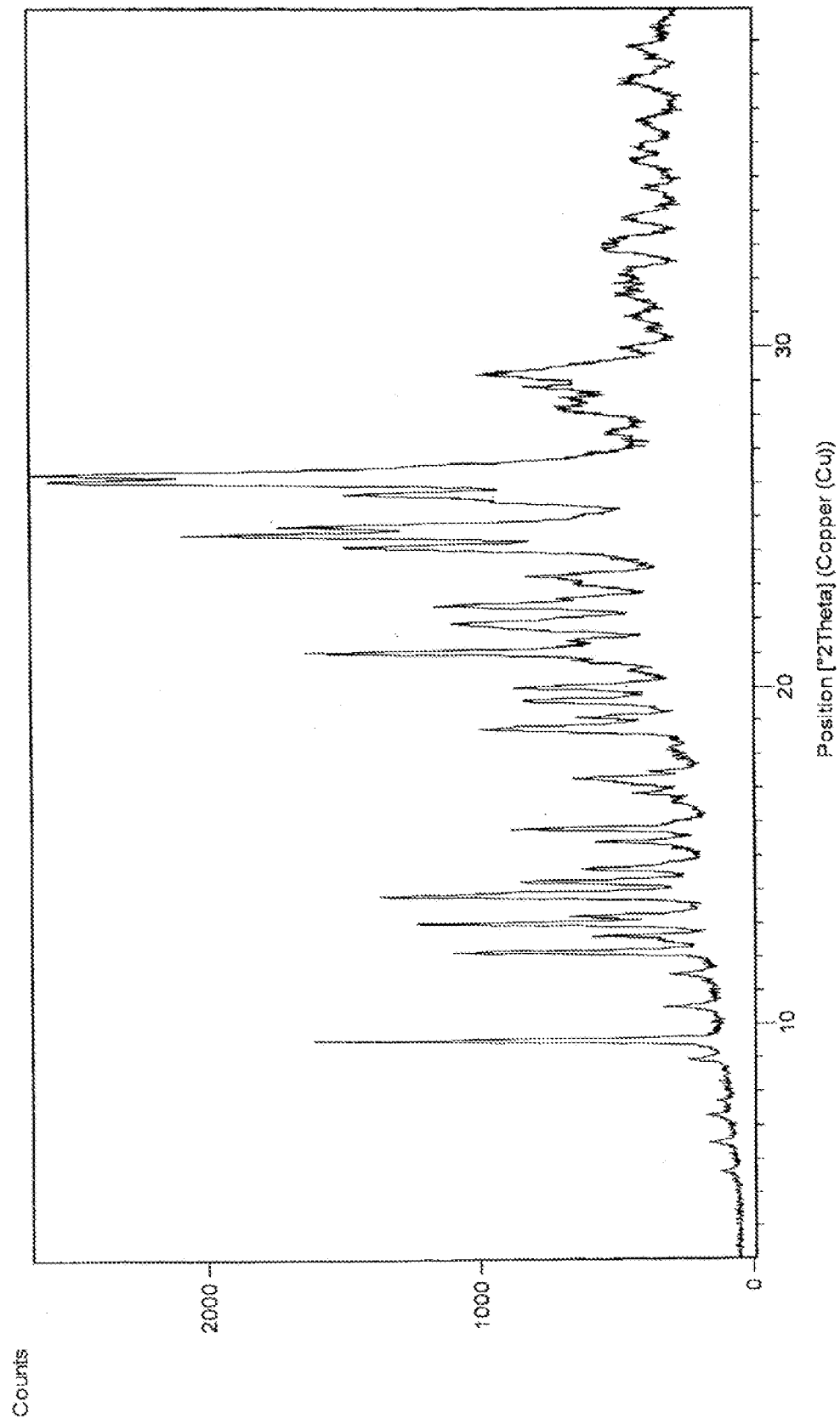
Figure 1: XRD Pattern of Crystalline Sorafenib Hydrochloride

Figure 1A: Table 1 – Peak Table for the XRD Pattern Depicted in Figure 1

| Pos [°2TH.] | d-spacing [Å] | Rel. Int. [%] |
|---|---|---|
| 5.64 | 15.67 | 3.08 |
| 6.50 | 13.60 | 3.16 |
| 7.30 | 12.11 | 3.21 |
| 8.93 | 9.90 | 5.41 |
| 9.53 | 9.28 | 35.99 |
| 10.52 | 8.40 | 5.10 |
| 11.49 | 7.70 | 8.39 |
| 12.17 | 7.27 | 34.58 |
| 12.64 | 6.70 | 10.40 |
| 13.03 | 6.79 | 28.31 |
| 13.24 | 6.89 | 14.44 |
| 13.82 | 6.40 | 44.07 |
| 14.26 | 6.21 | 26.70 |
| 14.65 | 6.05 | 18.65 |
| 15.45 | 5.74 | 9.58 |
| 15.82 | 5.60 | 20.20 |
| 16.86 | 5.26 | 10.49 |
| 17.29 | 5.13 | 17.29 |
| 18.76 | 4.73 | 22.50 |
| 19.11 | 4.64 | 15.55 |
| 19.65 | 4.52 | 29.01 |
| 19.98 | 4.44 | 22.43 |
| 21.00 | 4.22 | 43.75 |
| 21.85 | 4.06 | 49.03 |
| 22.36 | 3.98 | 25.74 |
| 23.26 | 3.82 | 27.58 |
| 24.10 | 3.69 | 94.71 |
| 24.46 | 3.63 | 68.36 |
| 24.71 | 3.60 | 47.88 |
| 25.67 | 3.47 | 48.01 |
| 26.00 | 3.42 | 80.18 |
| 26.24 | 3.39 | 100.00 |
| 27.48 | 3.25 | 26.72 |
| 28.08 | 3.18 | 29.96 |
| 28.80 | 3.10 | 20.81 |
| 29.20 | 3.05 | 52.22 |
| 29.96 | 2.98 | 23.04 |
| 30.86 | 2.90 | 21.82 |
| 32.30 | 2.77 | 32.62 |
| 32.84 | 2.73 | 36.52 |
| 33.15 | 2.70 | 25.12 |
| 33.73 | 2.66 | 33.55 |
| 34.68 | 2.59 | 18.06 |
| 35.46 | 2.53 | 24.55 |
| 36.66 | 2.45 | 32.83 |
| 37.84 | 2.38 | 30.27 |
| 38.83 | 2.32 | 21.79 |

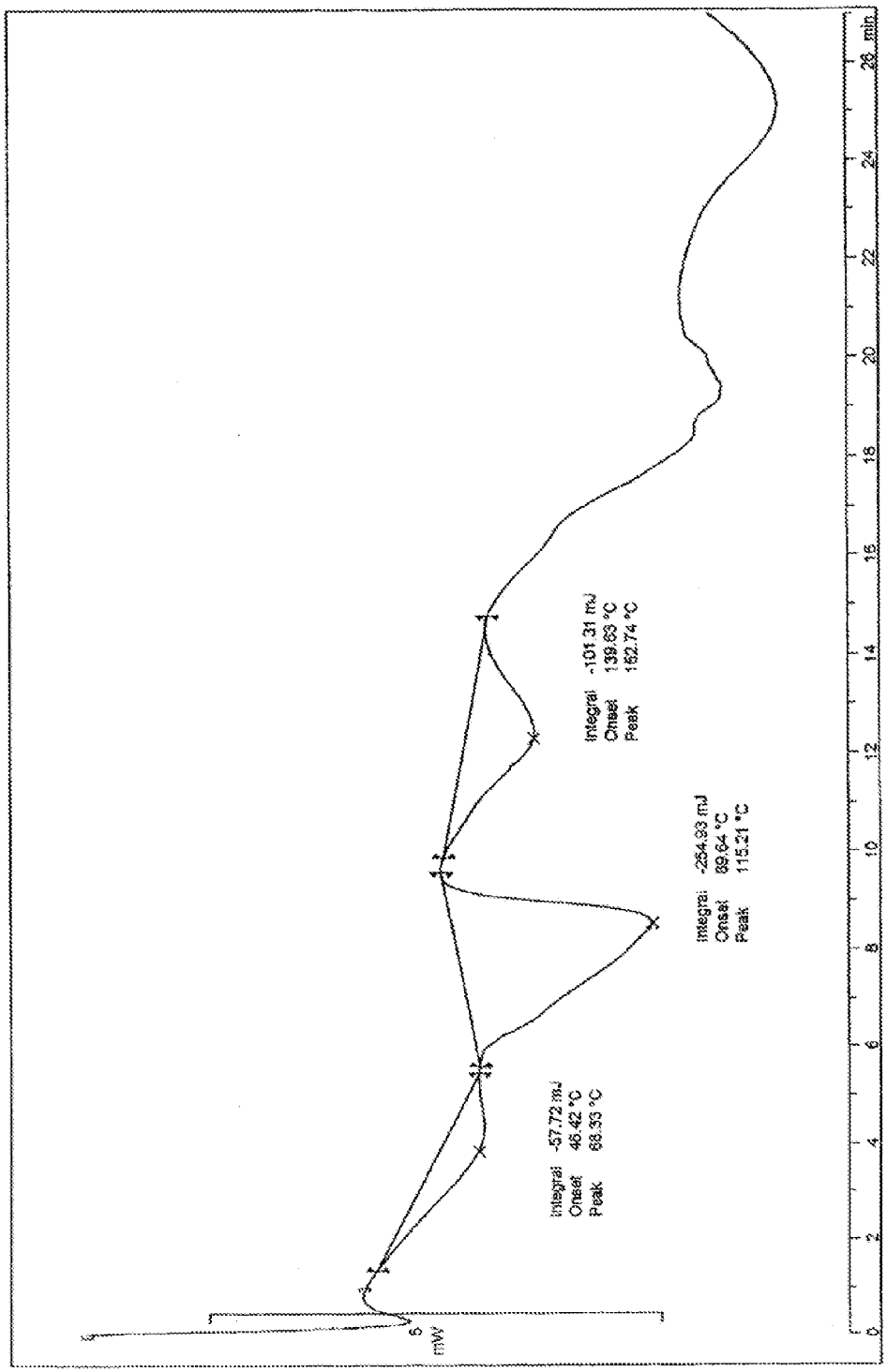
Figure 2: DSC Thermogram of Crystalline Sorafenib Hydrochloride

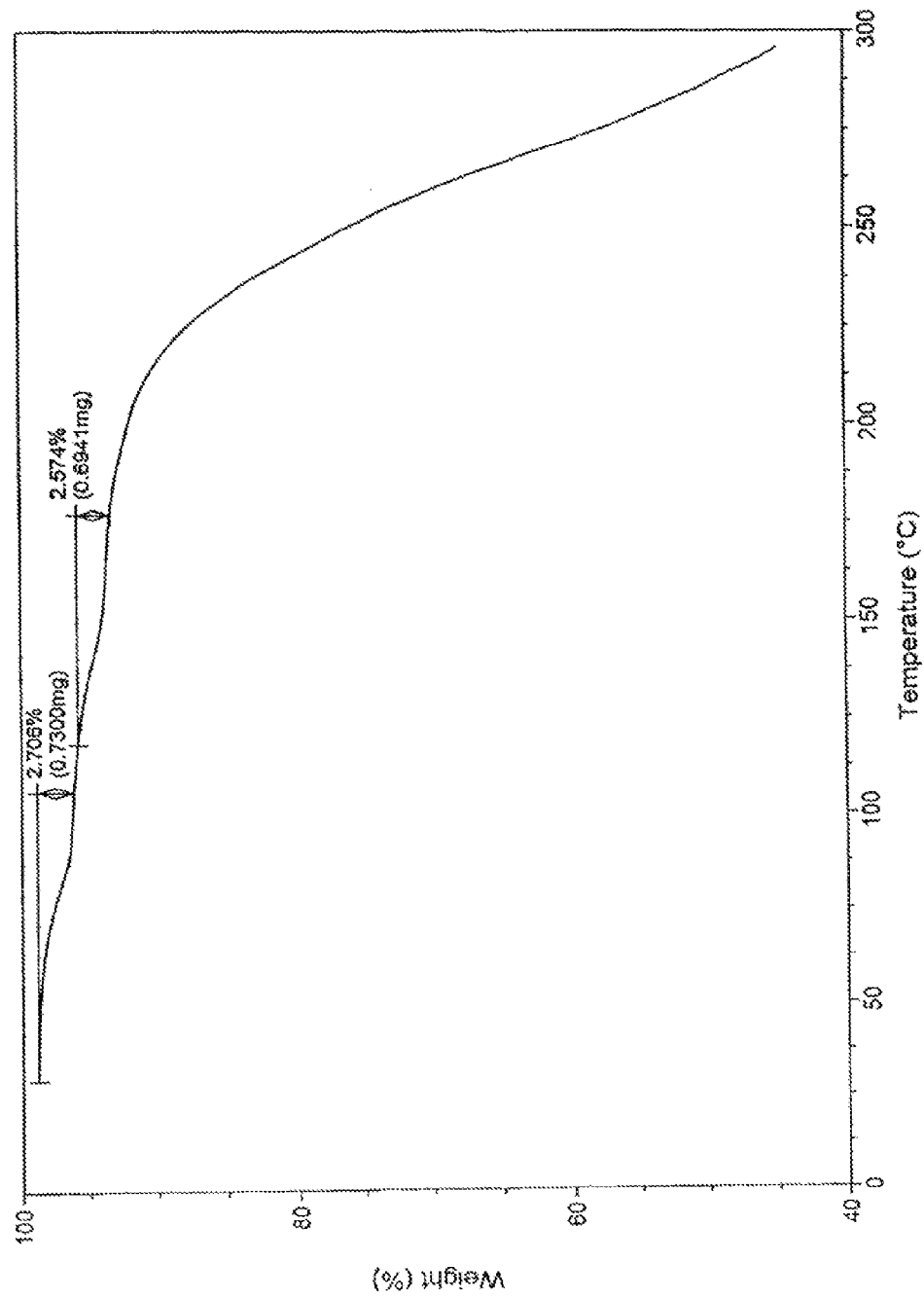
Figure 3: TGA Curve of Crystalline Sorafenib Hydrochloride

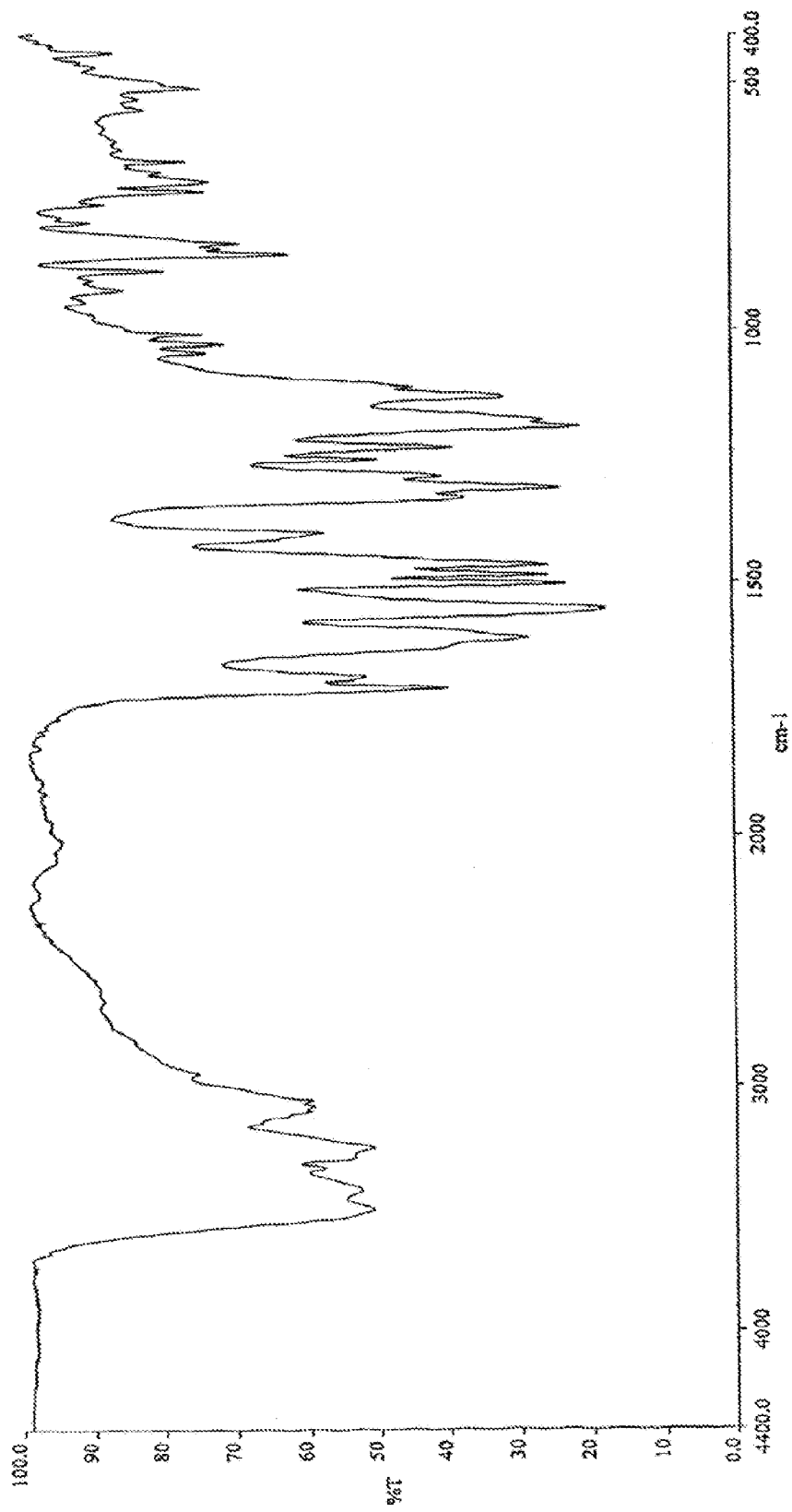

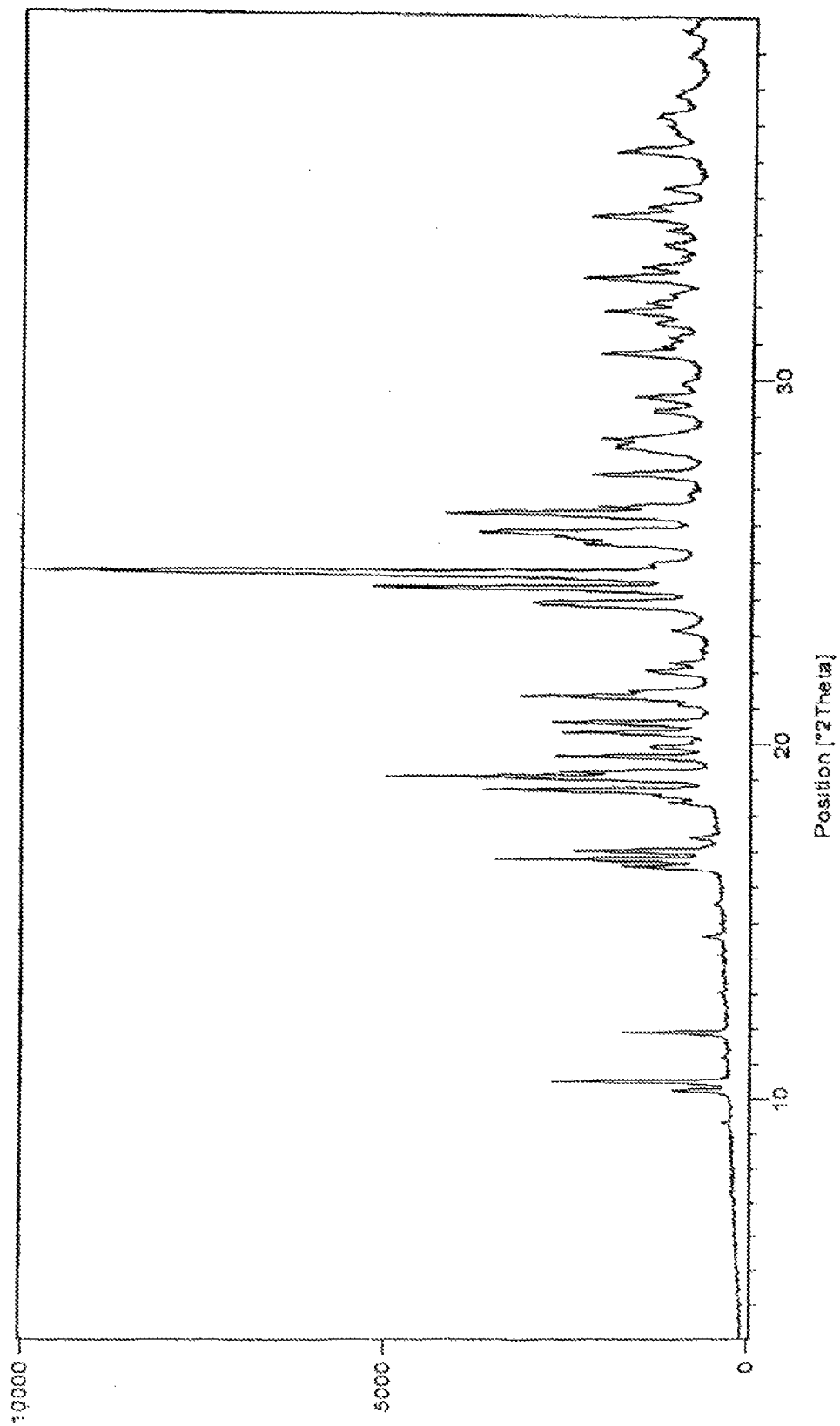
Figure 5: XRD Pattern of Crystalline Sorafenib Hydrobromide

Figure 5A: Table 2 – Peak Table for the XRD Pattern Depicted in Figure 5

| Pos [°2TH.] | d-spacing [Å] | Rel. Int. [%] | Pos [°2TH.] | d-spacing [Å] | Rel. Int. [%] |
| --- | --- | --- | --- | --- | --- |
| 9.32 | 9.49 | 1.37 | 25.46 | 3.50 | 20.80 |
| 10.25 | 8.63 | 8.42 | 25.79 | 3.45 | 32.56 |
| 10.51 | 8.41 | 23.76 | 26.26 | 3.39 | 39.83 |
| 11.91 | 7.43 | 15.27 | 26.48 | 3.36 | 18.85 |
| 14.64 | 6.05 | 4.35 | 27.36 | 3.26 | 19.88 |
| 15.54 | 5.70 | 2.55 | 28.13 | 3.17 | 16.51 |
| 16.58 | 5.35 | 15.41 | 28.34 | 3.14 | 18.94 |
| 16.78 | 5.28 | 33.06 | 29.12 | 3.07 | 11.37 |
| 17.02 | 5.21 | 22.22 | 29.50 | 3.03 | 13.36 |
| 17.40 | 5.10 | 5.78 | 29.90 | 2.99 | 7.54 |
| 18.37 | 4.83 | 8.98 | 30.68 | 2.91 | 18.87 |
| 18.69 | 4.74 | 35.09 | 31.17 | 2.87 | 9.11 |
| 19.03 | 4.66 | 47.40 | 31.53 | 2.84 | 11.33 |
| 19.20 | 4.62 | 23.65 | 31.85 | 2.81 | 18.44 |
| 19.62 | 4.52 | 25.08 | 32.76 | 2.73 | 21.68 |
| 19.89 | 4.46 | 11.65 | 33.07 | 2.71 | 13.32 |
| 20.28 | 4.38 | 23.16 | 33.66 | 2.66 | 10.11 |
| 20.55 | 4.32 | 25.31 | 34.08 | 2.63 | 9.36 |
| 21.28 | 4.17 | 28.76 | 34.46 | 2.60 | 19.91 |
| 21.44 | 4.14 | 14.17 | 34.73 | 2.58 | 12.51 |
| 22.02 | 4.04 | 12.24 | 35.24 | 2.55 | 10.19 |
| 22.22 | 4.00 | 8.76 | 36.23 | 2.48 | 16.93 |
| 23.13 | 3.84 | 8.74 | 37.25 | 2.41 | 10.88 |
| 23.77 | 3.73 | 25.43 | 37.80 | 2.38 | 8.61 |
| 23.87 | 3.72 | 28.16 | 38.93 | 2.31 | 6.77 |
| 24.24 | 3.67 | 49.64 | 39.60 | 2.28 | 7.60 |
| 24.62 | 3.61 | 100.00 | | | |
| 24.95 | 3.57 | 11.46 | | | |

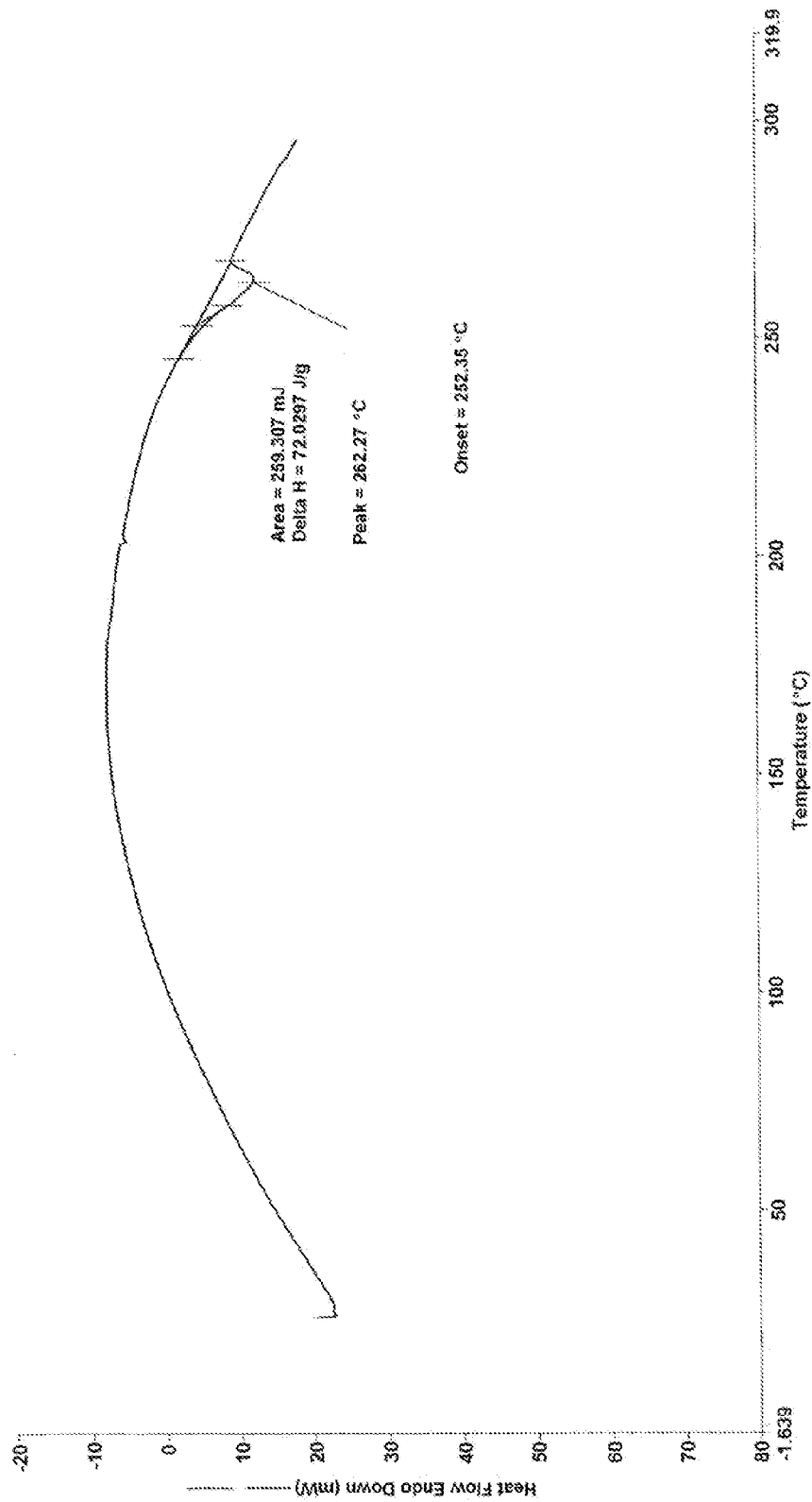
Figure 6: DSC Thermogram of Crystalline Sorafenib Hydrobromide

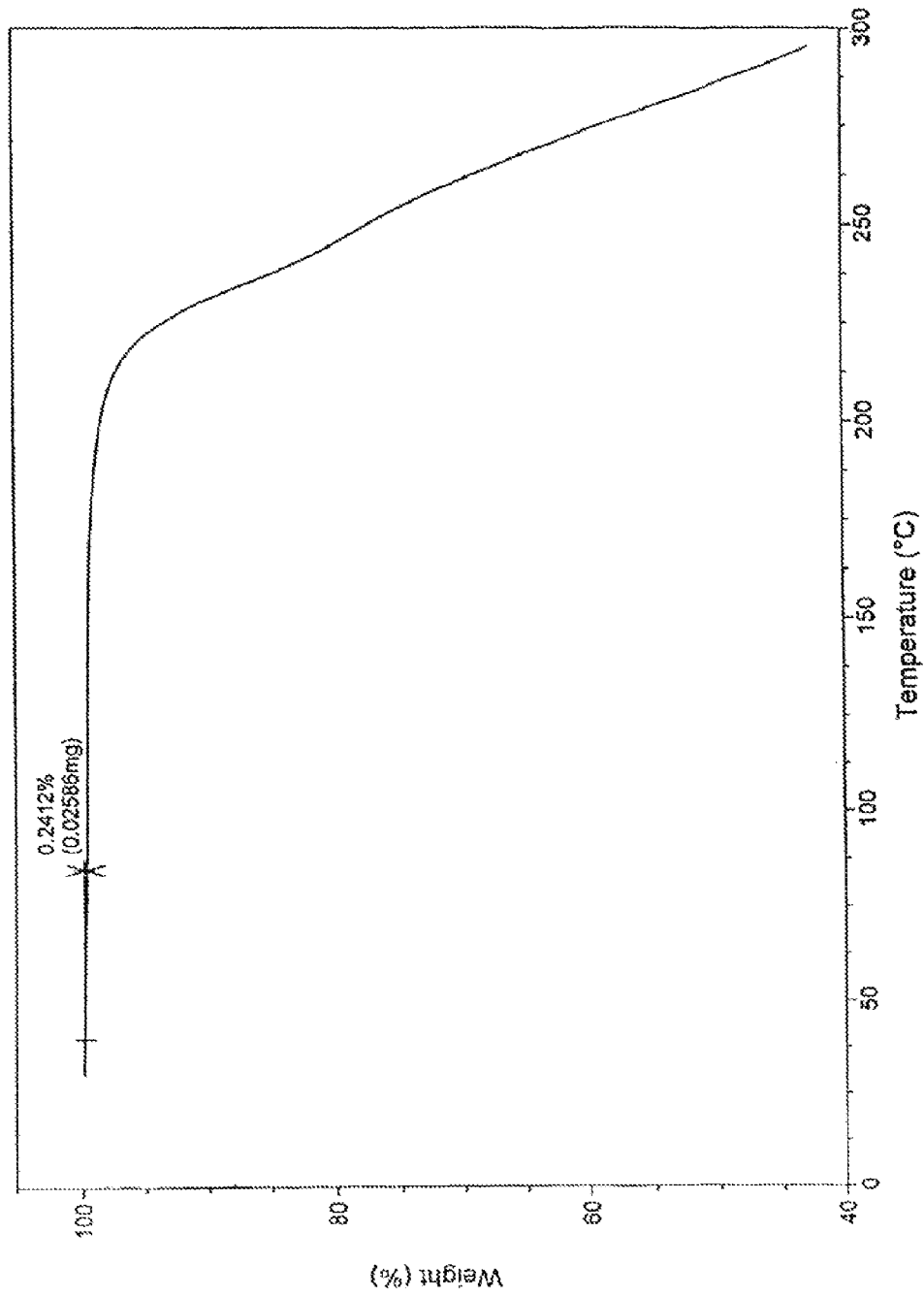
Figure 7: TGA Curve of Crystalline Sorafenib Hydrobromide

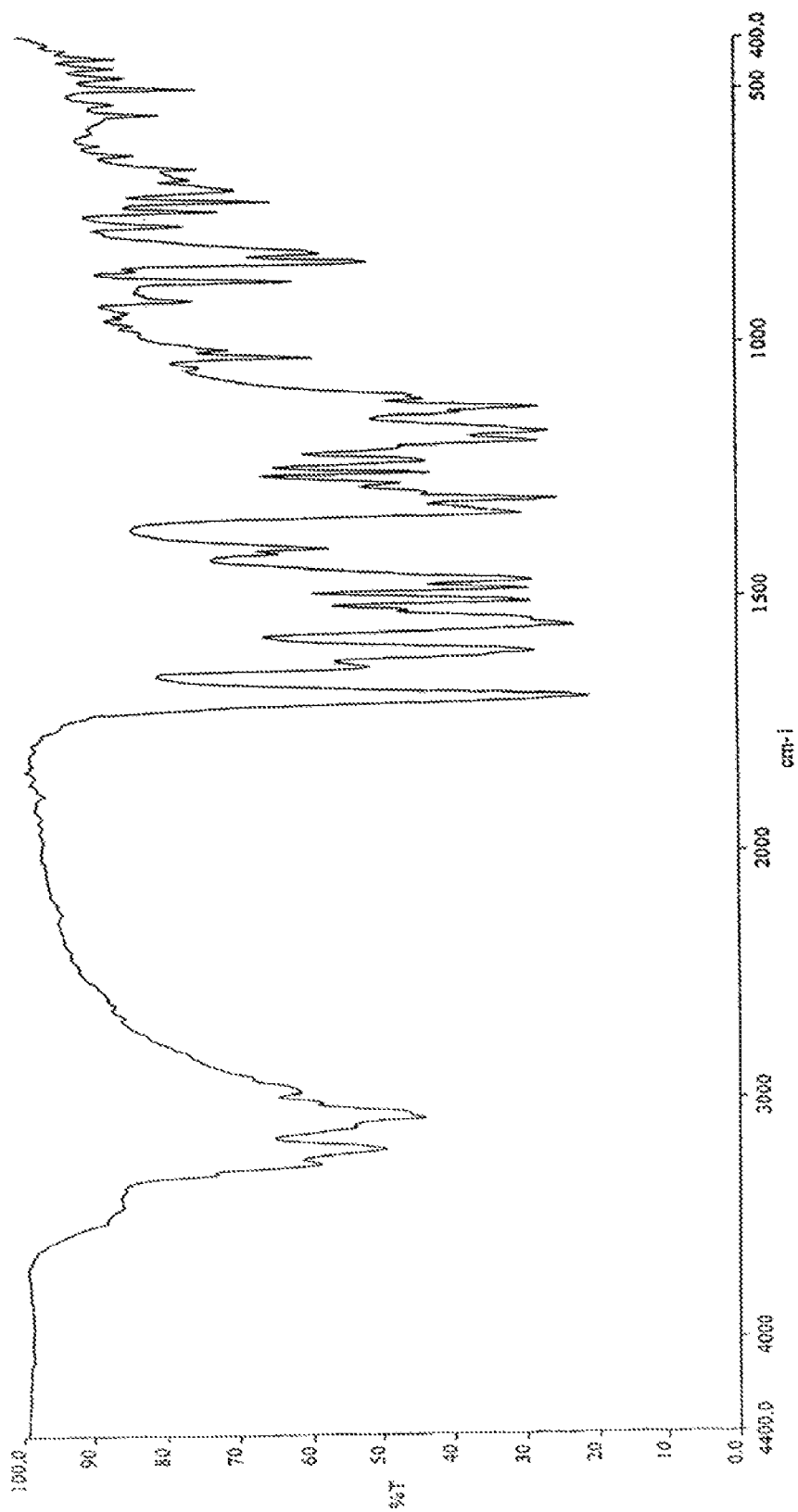
Figure 8: IR Spectrum of Crystalline Sorafenib Hydrobromide

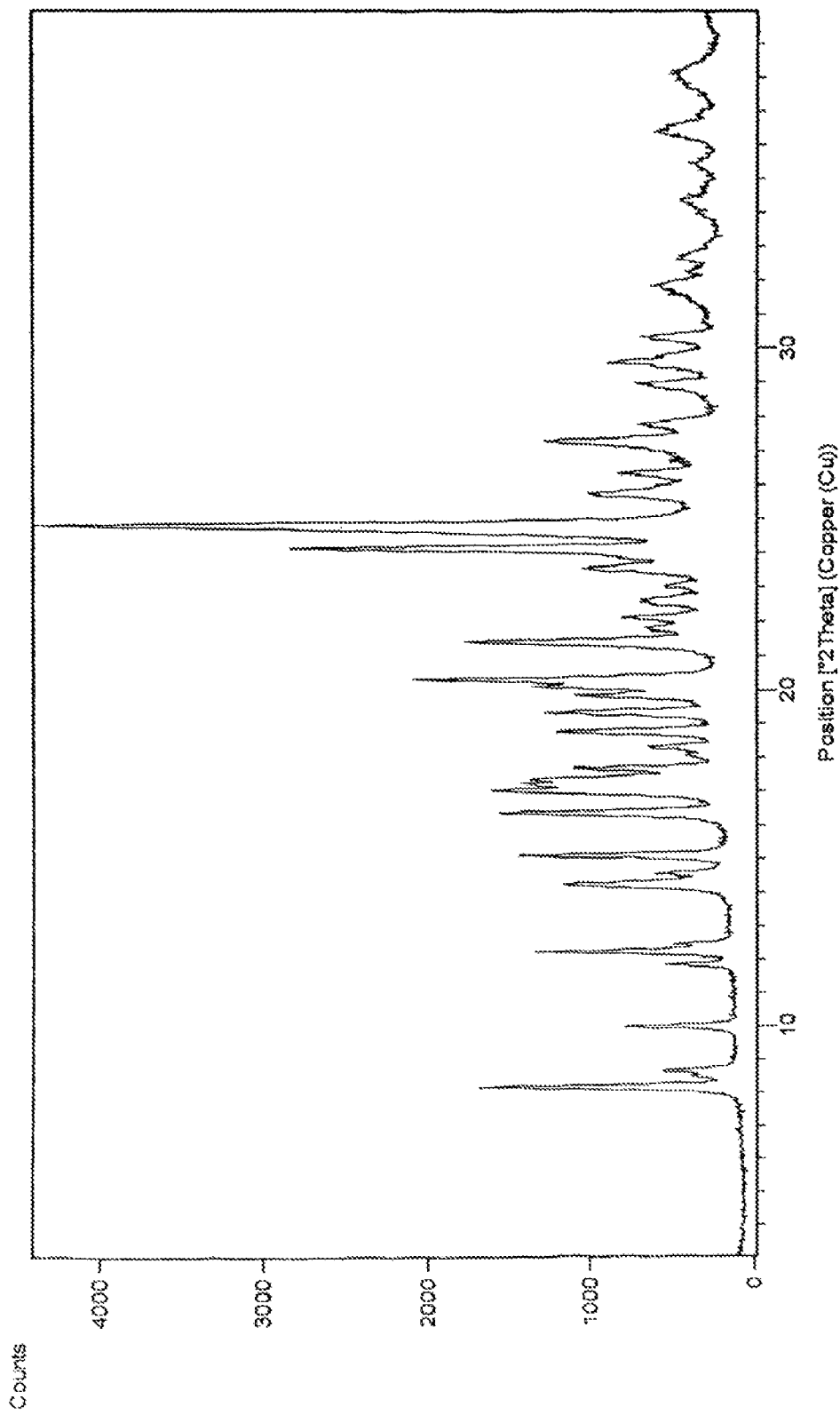
Figure 9: XRD Pattern of Crystalline Sorafenib Methanesulphonate

Figure 9A: Table 3 – Peak Table for the XRD Pattern Depicted in Figure 9

| Pos [°2TH.] | d-spacing [Å] | Rel. Int. [%] |
|---|---|---|
| 8.18 | 10.80 | 22.34 |
| 8.70 | 10.17 | 6.23 |
| 10.02 | 8.83 | 9.67 |
| 11.88 | 7.45 | 4.13 |
| 12.28 | 7.21 | 16.90 |
| 12.49 | 7.09 | 3.55 |
| 14.25 | 6.21 | 18.91 |
| 14.58 | 6.07 | 6.08 |
| 15.12 | 5.85 | 21.18 |
| 16.37 | 5.41 | 29.97 |
| 17.01 | 5.20 | 26.98 |
| 17.40 | 5.10 | 19.24 |
| 17.70 | 5.01 | 13.49 |
| 18.32 | 4.84 | 5.84 |
| 18.77 | 4.73 | 19.86 |
| 19.34 | 4.58 | 20.88 |
| 19.85 | 4.47 | 15.25 |
| 20.09 | 4.41 | 13.78 |
| 20.31 | 4.37 | 22.81 |
| 21.41 | 4.15 | 35.69 |
| 21.78 | 4.08 | 9.19 |
| 22.10 | 4.02 | 12.06 |
| 22.63 | 3.93 | 16.52 |
| 23.01 | 3.86 | 6.98 |
| 23.51 | 3.78 | 13.90 |
| 24.13 | 3.68 | 49.80 |
| 24.80 | 3.59 | 100.00 |
| 25.71 | 3.46 | 19.03 |
| 26.34 | 3.38 | 13.31 |
| 22.29 | 3.27 | 14.89 |
| 27.78 | 3.21 | 13.37 |
| 28.95 | 3.08 | 18.27 |
| 29.53 | 3.02 | 9.97 |
| 30.34 | 2.95 | 10.28 |
| 31.86 | 2.81 | 17.00 |
| 32.70 | 2.74 | 6.37 |
| 34.33 | 2.61 | 6.40 |
| 35.44 | 2.53 | 5.28 |
| 36.35 | 2.47 | 18.08 |
| 38.13 | 2.36 | 10.78 |

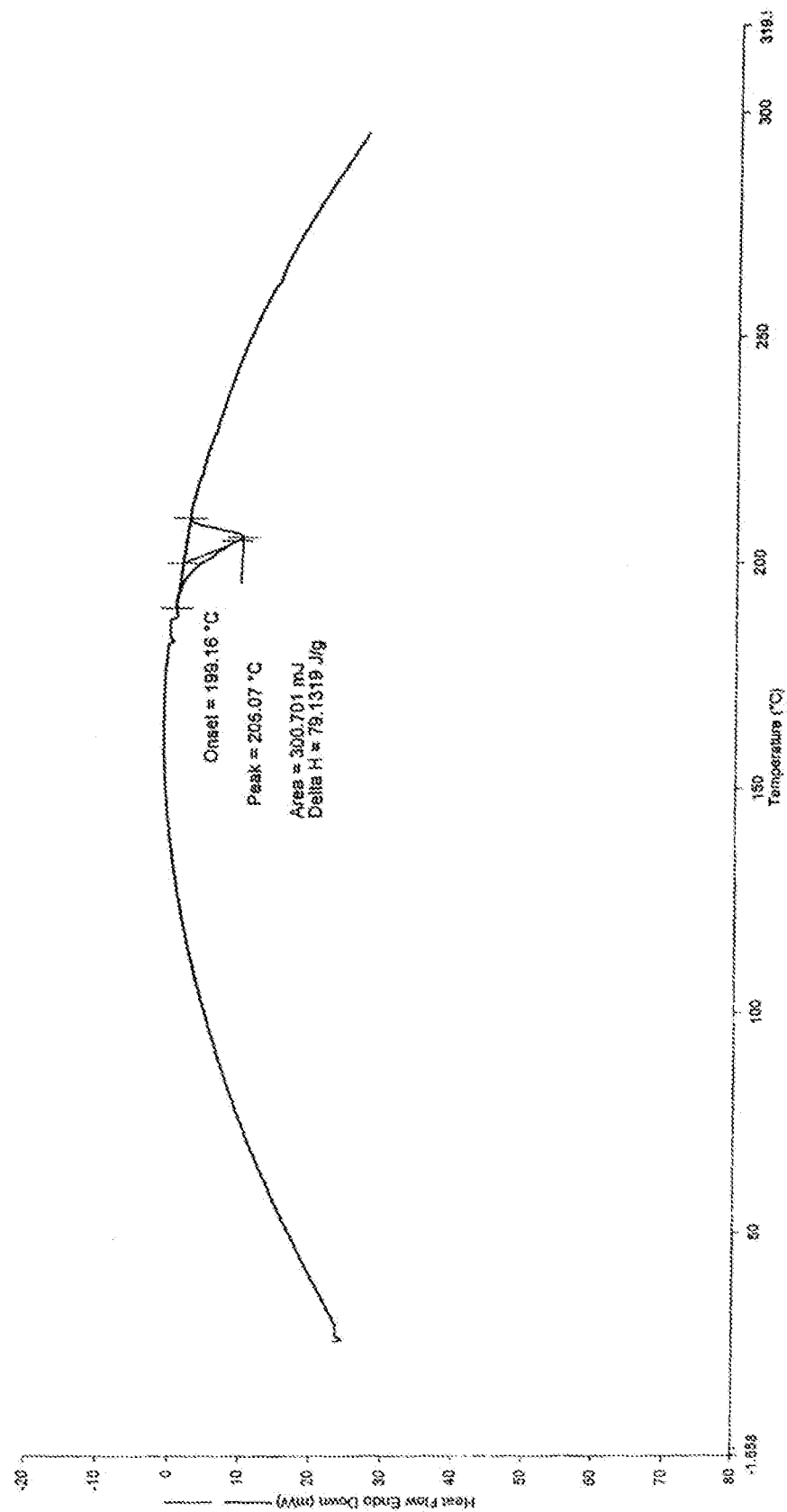
Figure 10: DSC Thermogram of Crystalline Sorafenib Methanesulphonate

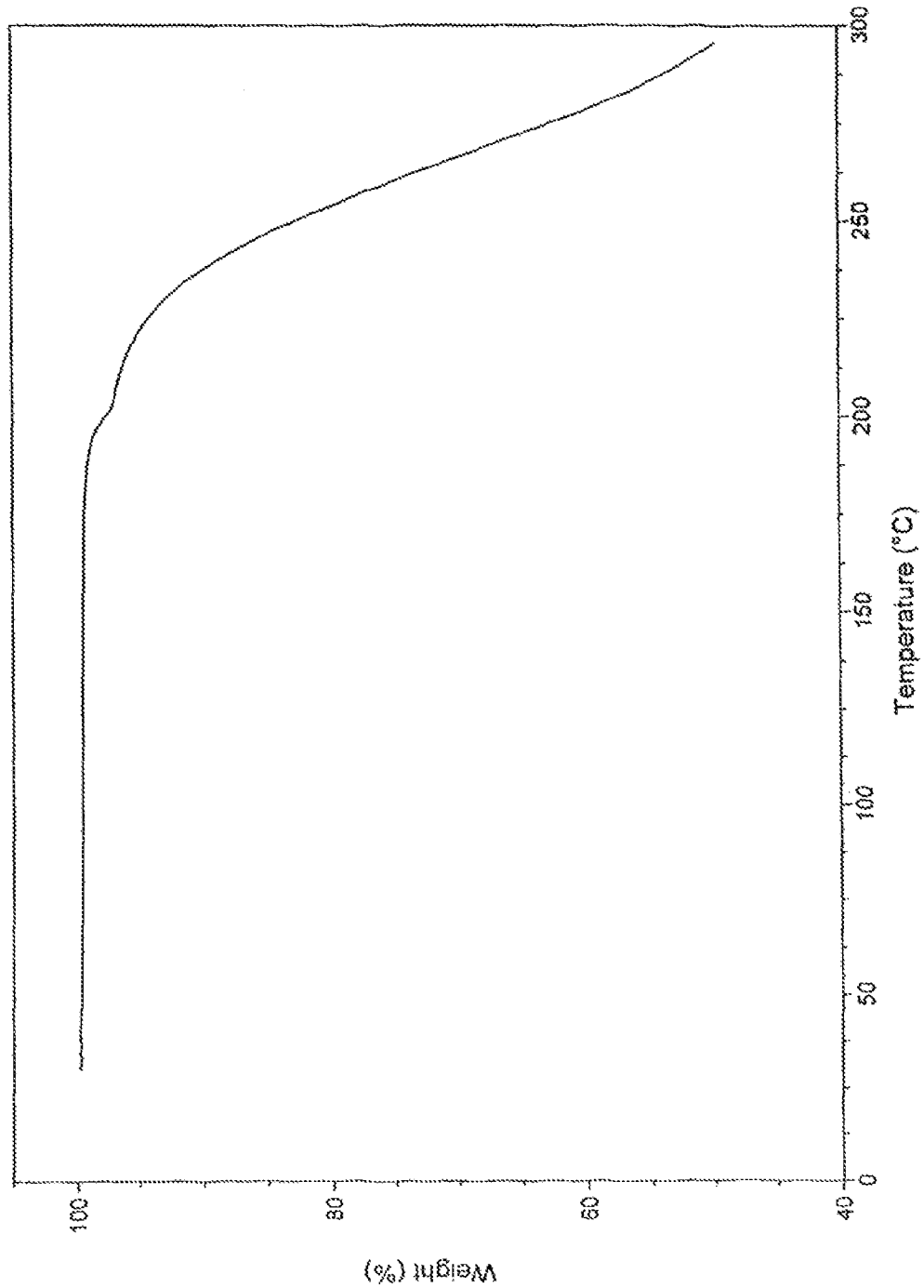

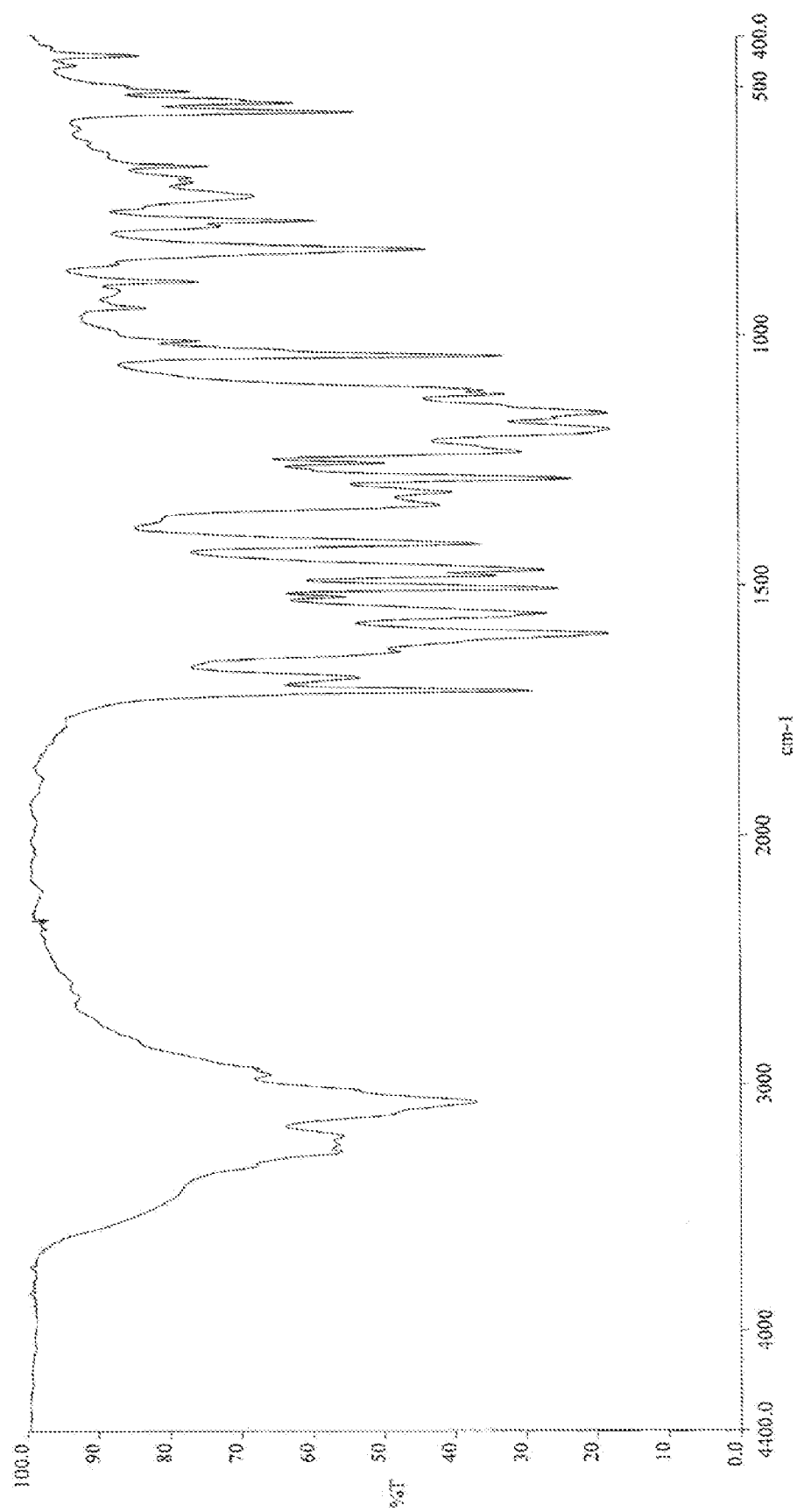

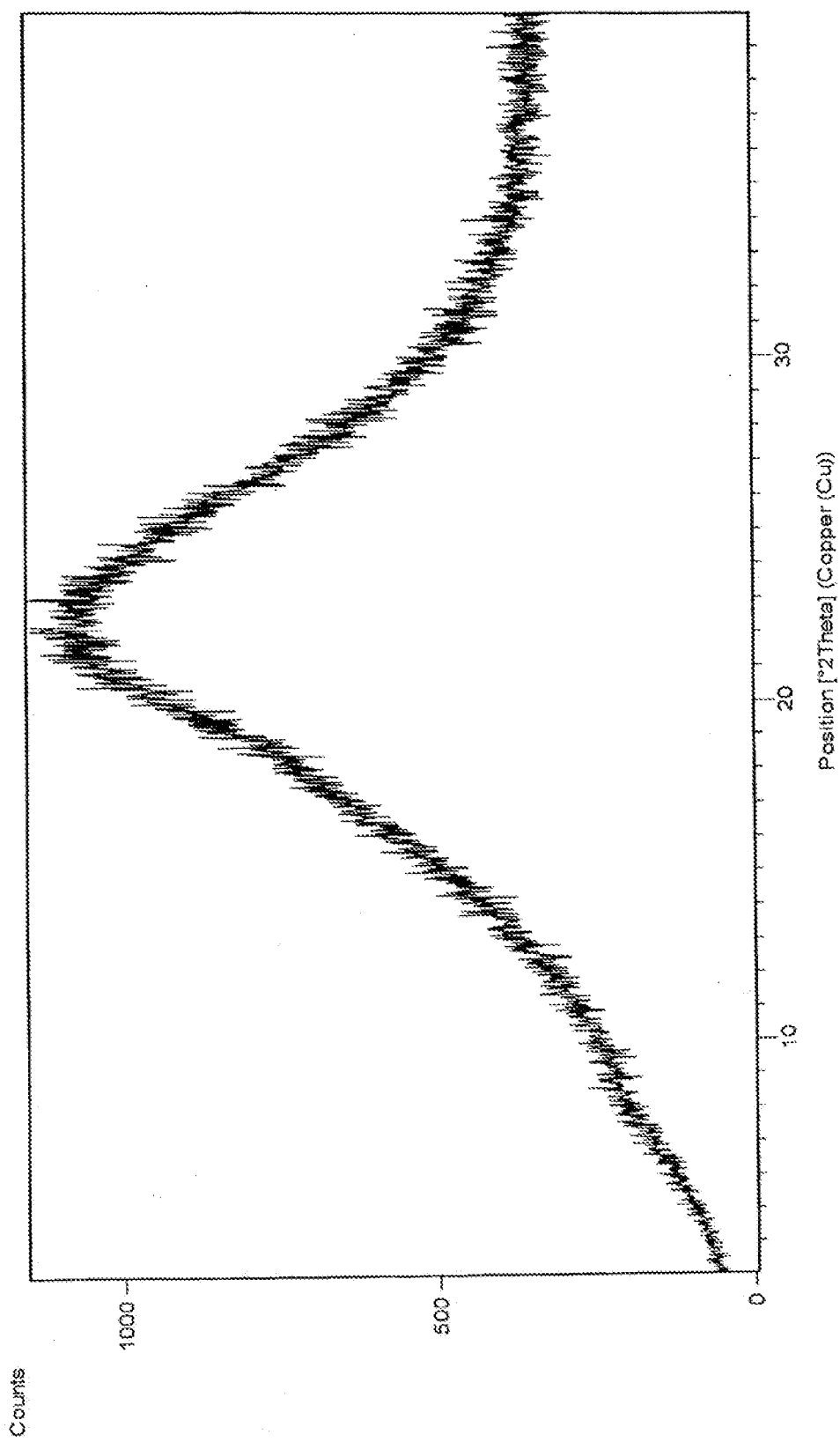
Figure 13: XRD Pattern of Amorphous Sorafenib Sulphate

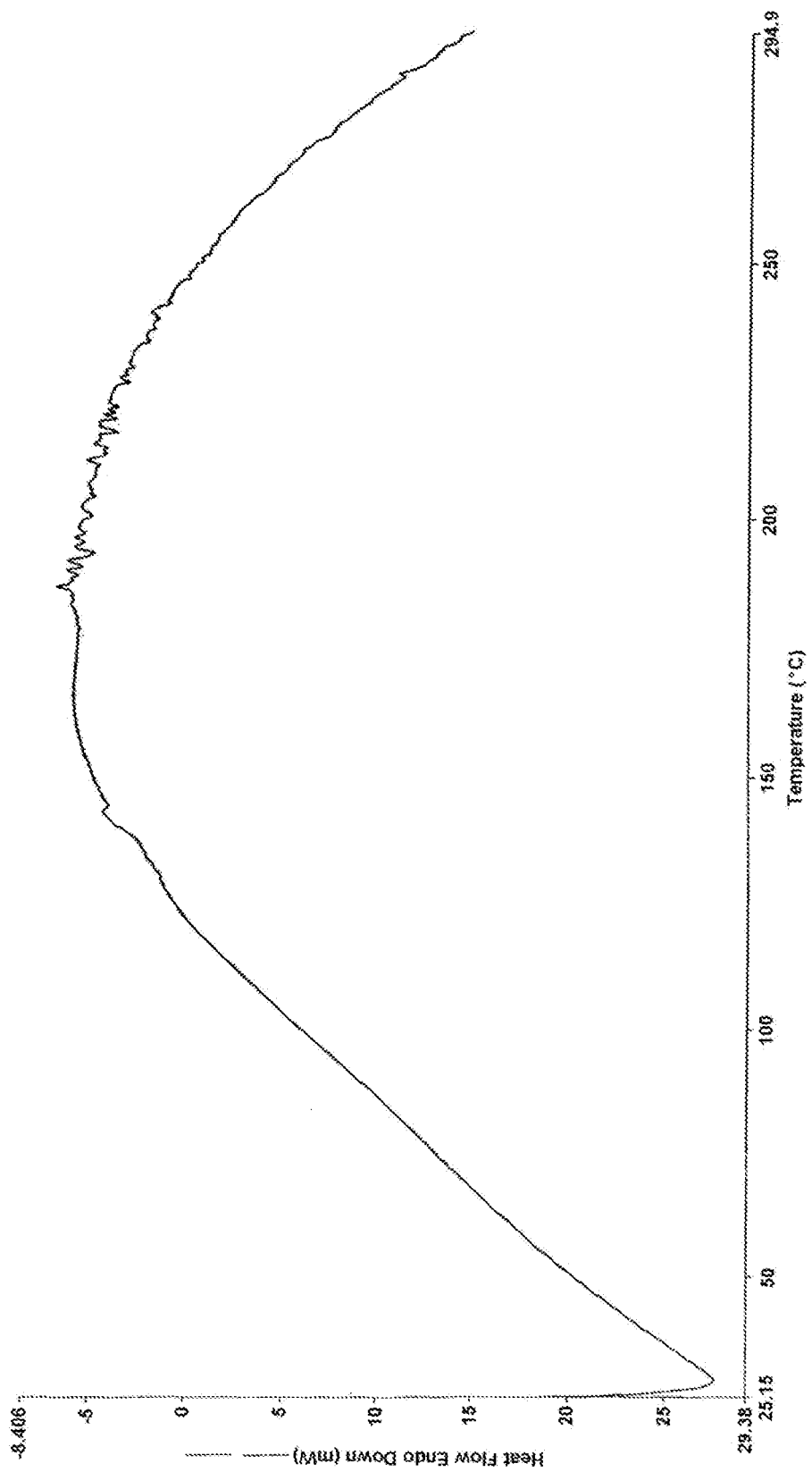
Figure 14: DSC Thermogram of Amorphous Sorafenib Sulphate

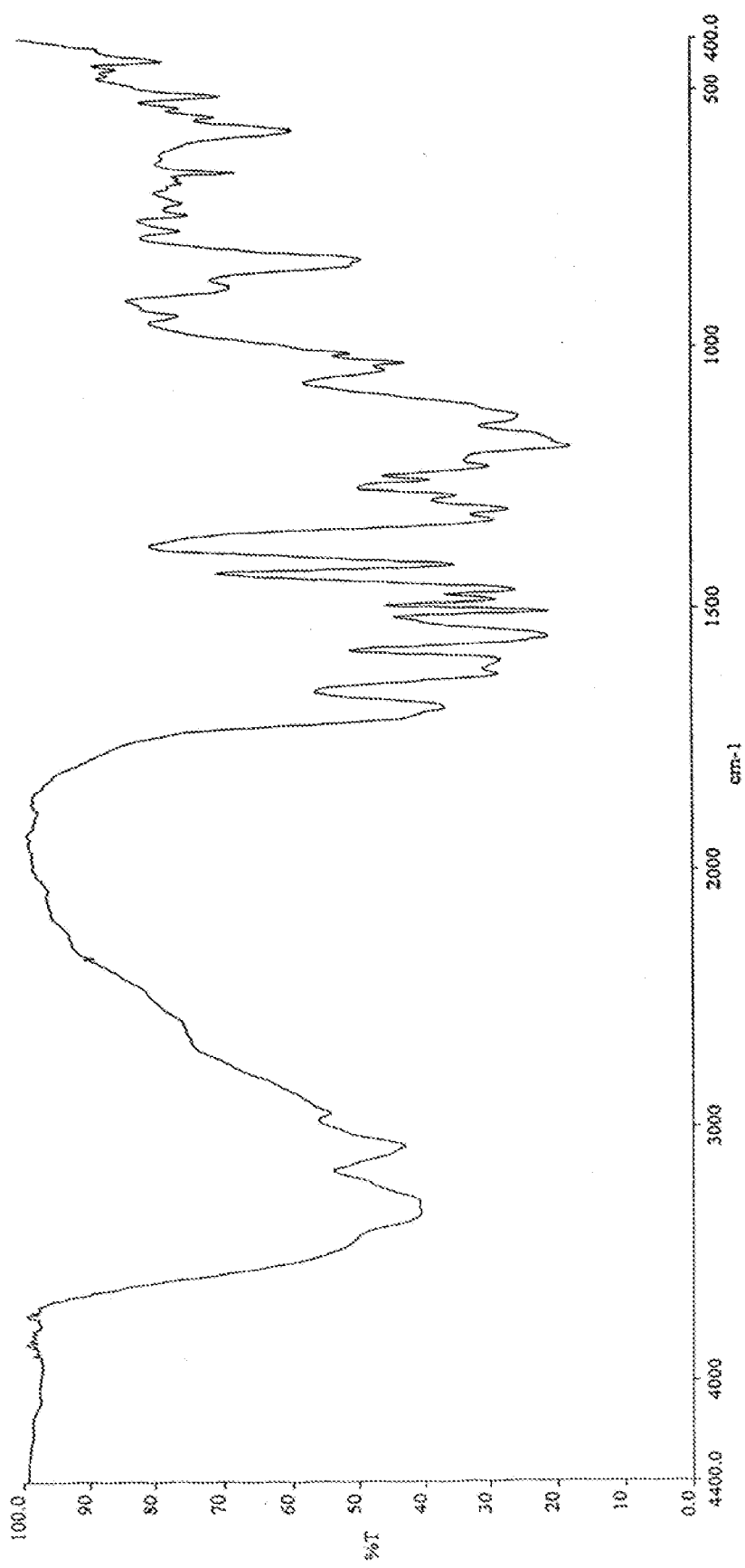
Figure 15: TGA Curve of Amorphous Sorafenib Sulphate

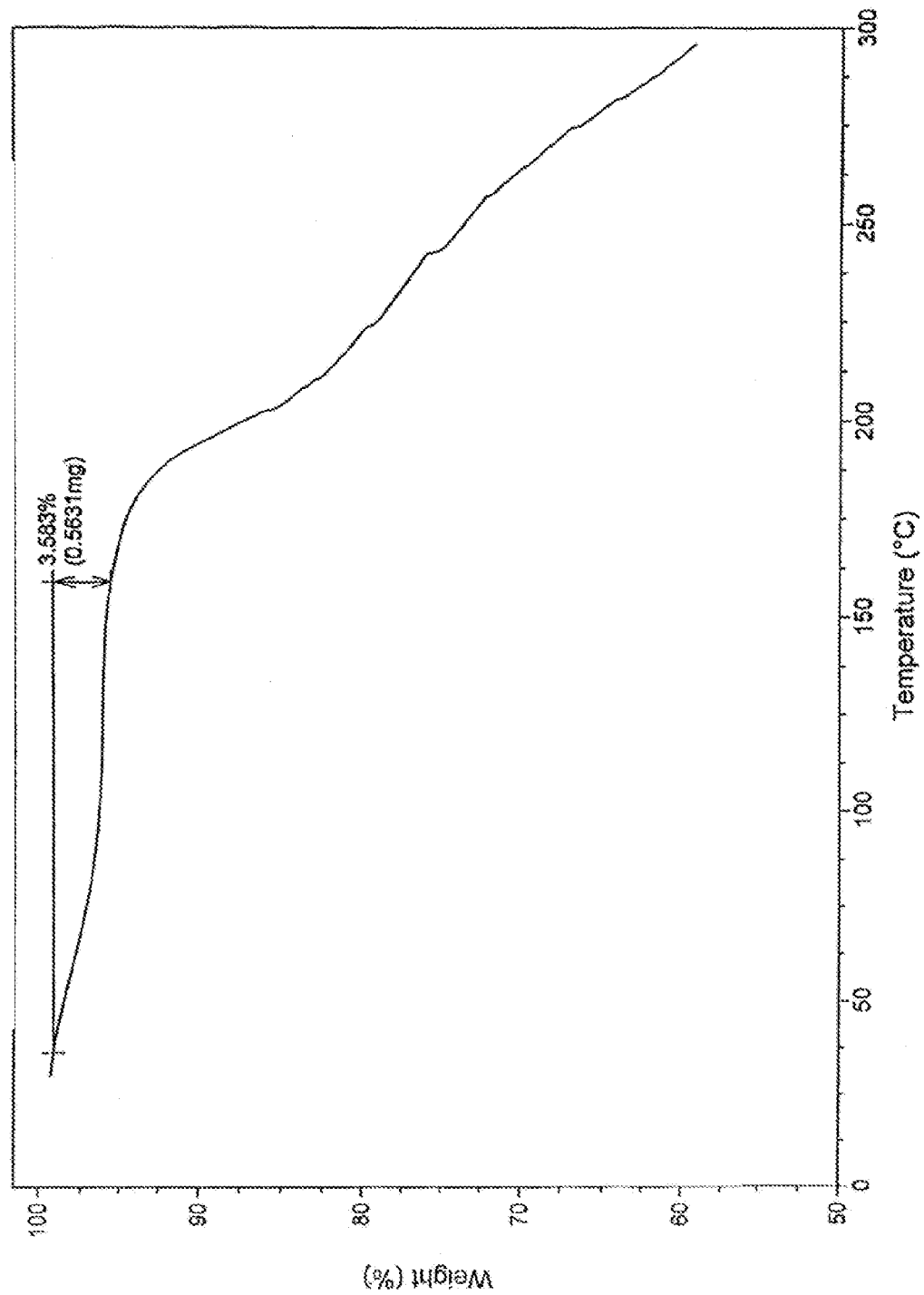
Figure 16: IR Spectrum of Amorphous Sorafenib Sulphate

POLYMORPHS OF SORAFENIB ACID ADDITION SALTS

FIELD OF THE INVENTION

The present invention provides amorphous and crystalline forms of sorafenib acid addition salts, process for their preparation, pharmaceutical compositions comprising them and their use for the treatment of cancer. The present invention also provides a process for the preparation of sorafenib acid addition salts.

BACKGROUND OF THE INVENTION

Sorafenib is an inhibitor of the enzyme Raf kinase known from WO 00/42012. It is chemically 4-(4-{3-[4-Chloro-3-(trifluoromethyl)phenyl]ureido }phenoxy)-$N^2$-methylpyridine-2-carboxamide having the structure as represented by Formula I.

Formula I

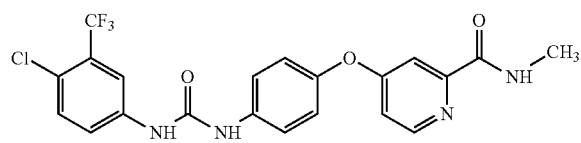

Sorafenib is marketed in the United States as its tosylate salt of Formula II under the brand name Nexavar®.

Formula II

Several acid addition salts of sorafenib are disclosed in WO 00/42012.

Processes for the preparation of sorafenib tosylate are disclosed in WO 2006/034796, WO 2006/034797, WO 2009/034308, WO 2009/054004, WO 2009/106825 and WO 2009/092070, which are incorporated herein by reference. Besides sorafenib tosylate, no other salt of sorafenib has been prepared in the literature.

SUMMARY OF THE INVENTION

The present invention provides amorphous and crystalline forms of sorafenib acid addition salts, a process for their preparation, pharmaceutical compositions comprising them and their use for the treatment of cancer. The present invention also provides processes for the preparation of sorafenib acid addition salts.

A first aspect of the present invention provides crystalline form of sorafenib hydrochloride of Formula III.

Formula III

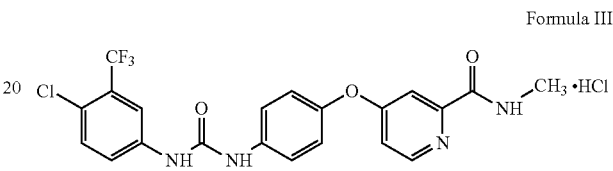

A second aspect of the present invention provides crystalline form of sorafenib hydrobromide of Formula IV.

Formula IV

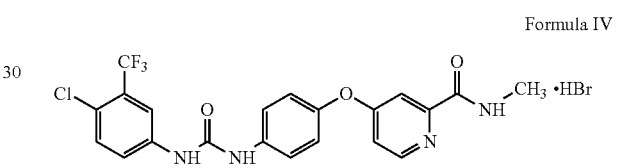

A third aspect of the present invention provides crystalline form of sorafenib methane sulphonate of Formula V.

Formula V

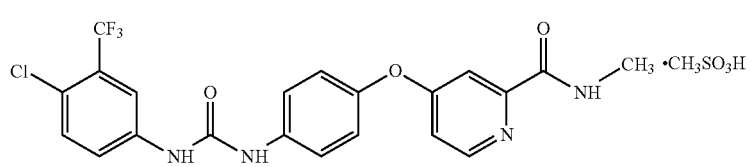

A fourth aspect of the present invention provides amorphous form of sorafenib sulphate of Formula VI.

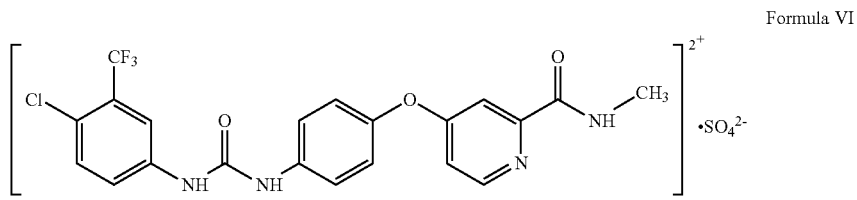

Formula VI

A fifth aspect of the present invention provides process for the preparation of acid addition salts of sorafenib of Formula VII

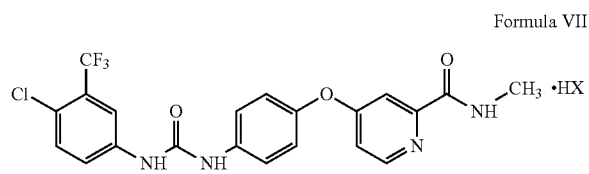

Formula VII wherein HX is an acid addition salt as defined herein. comprising contacting sorafenib free base of Formula I

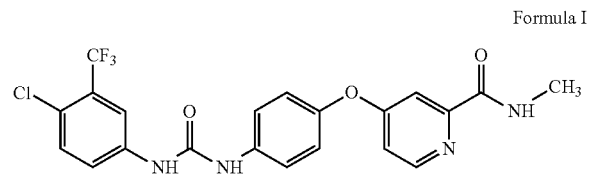 [SMILES: CNC(=O)c1cc(Oc2ccc(NC(=O)Nc3ccc(Cl)c(C(F)(F)F)c3)cc2)ccn1]

Formula I with an acid of Formula HX

A sixth aspect of the present invention provides use of sorafenib acid addition salts for the preparation of high purity sorafenib base.

A seventh aspect of the present invention provides use of a sorafenib acid addition salt as an intermediate for the preparation of sorafenib tosylate.

An eighth aspect of the present invention provides pharmaceutical compositions comprising sorafenib acid addition salts of Formula VII and one or more pharmaceutically acceptable carriers, diluents or excipients.

A ninth aspect of the present invention provides use of sorafenib acid addition salts of Formula VII for the treatment of cancer.

A tenth aspect of the present invention provides pharmaceutical composition comprising sorafenib acid addition salts selected from crystalline sorafenib hydrochloride of Formula III, crystalline sorafenib hydrobromide of Formula IV, crystalline sorafenib methane sulphonate of Formula V, or amorphous sorafenib sulphate of Formula VI, and one or more pharmaceutically acceptable carriers, diluents or excipients.

An eleventh aspect of the present invention provides use of sorafenib acid addition salts selected from crystalline sorafenib hydrochloride of Formula III, crystalline sorafenib hydrobromide of Formula V, crystalline sorafenib methane sulphonate of Formula V, or amorphous sorafenib sulphate of Formula VI for the treatment of cancer.

The present invention may involve one or more of the following embodiments.

In one embodiment, crystalline sorafenib hydrochloride of Formula III may be characterized by X-ray diffraction (XRD) peaks having d-spacing values at 3.69, 3.63, 3.42, 3.39 and 3.05 Å. It may be further characterized by XRD peaks having d-spacing values at 6.40, 4.22, 4.06 and 3.60 Å. It may also be characterized by a Differential Scanning Thermogram (DSC) having endotherms at about 68.33° C., 115.21° C. and 152.74° C. Crystalline sorafenib hydrochloride of Formula III may also be characterized by XRD spectrum, DSC thermogram, Thermogravimetric Analysis (TGA) and (Infra-Red) IR spectra as depicted in FIGS. 1, 2, 3 and 4, respectively. Table 1 provides the 2θ, d-spacing values and relative intensity of XRD peaks of sorafenib hydrochloride.

In another embodiment, crystalline sorafenib hydrobromide may be characterized by XRD peaks having d-spacing values at 4.74, 4.66, 3.67, 3.61 and 3.39 Å. It may be further characterized by XRD peaks having d-spacing values at 5.28, 4.17, 3.73, 3.72 and 3.45 Å. It may also be characterized by a DSC thermogram having endotherm at about 262.27° C. Crystalline sorafenib hydrobromide of Formula IV may also be characterized by XRD spectrum, DSC thermogram, TGA and IR spectra as depicted in FIGS. 5, 6, 7 and 8, respectively. Table 2 provides the 2θ, d-spacing values and relative intensity of XRD peaks of sorafenib hydrobromide.

In another embodiment, crystalline sorafenib methane sulphonate of Formula V may be characterized by XRD peaks having d-spacing values at 5.41, 5.20, 4.14, 3.68 and 3.58 Å. It may be further characterized by XRD peaks having d-spacing values at 10.80, 5.85, 5.20, 4.58 and 4.41 Å. It may also be characterized by a DSC thermogram having endotherm at about 205.07° C. Crystalline sorafenib methane sulphonate of Formula V may also be characterized by XRD spectrum, DSC thermogram, TGA and IR spectra as depicted in FIGS. 9, 10, 11 and 12, respectively. Table 3 provides the 2θ, d-spacing values and relative intensity of XRD peaks of sorafenib methane sulphonate.

In another embodiment, amorphous sorafenib sulphate of Formula VI may be characterized by XRD spectrum, DSC thermogram, TGA and IR spectrum as depicted in FIGS. 13, 14, 15 and 16, respectively.

BRIEF DESCRIPTION OF THE FIGURES

FIG. 1: XRD pattern of crystalline sorafenib hydrochloride.
FIG. 2: DSC thermogram of crystalline sorafenib hydrochloride.
FIG. 3: TGA curve of crystalline sorafenib hydrochloride.
FIG. 4: IR spectrum of crystalline sorafenib hydrochloride.
FIG. 5: XRD pattern of crystalline sorafenib hydrobromide.
FIG. 6: DSC thermogram of crystalline sorafenib hydrobromide.
FIG. 7: TGA curve of crystalline sorafenib hydrobromide.
FIG. 8: IR spectrum of crystalline sorafenib hydrobromide.

FIG. 9: XRD pattern of crystalline sorafenib methanesulphonate.

FIG. 10: DSC thermogram of crystalline sorafenib methanesulphonate.

FIG. 11: TGA curve of crystalline sorafenib methanesulphonate.

FIG. 12: IR spectrum of crystalline sorafenib methanesulphonate.

FIG. 13: XRD pattern of amorphous sorafenib sulphate.

FIG. 14: DSC thermogram of amorphous sorafenib sulphate.

FIG. 15: TGA curve of amorphous sorafenib sulphate.

FIG. 16: IR spectrum of amorphous sorafenib sulphate.

DETAILED DESCRIPTION OF THE INVENTION

Crystalline sorafenib hydrochloride of Formula III may be characterized by XRD peaks at about 24.10±0.2° 2θ (d-spacing at 3.69 Å), 24.46±0.2° 2θ (3.63 Å), 26.00±0.2° 2θ (3.42 Å), 26.24±0.2° 2θ (3.39 Å) and 29.20±0.2° 2θ (3.05 Å). It may be further characterized by XRD peaks at about 13.82 (6.40 Å), 21.00 (4.22 Å), 21.85 (4.06 Å) and 24.71 (3.60 Å)±0.2 degrees 2θ. Crystalline sorafenib hydrochloride of Formula III may also be characterized by a DSC thermogram having endotherms at about 68.33° C., 115.21° C. and 152.74° C. Crystalline sorafenib hydrochloride of Formula III may also be characterized by XRD spectrum, DSC thermogram, TGA and IR spectrum as depicted in FIGS. 1, 2, 3 and 4, respectively.

Crystalline sorafenib hydrobromide of Formula IV may be characterized by peaks in the powder X-ray diffraction pattern at about 18.69±0.2° 2θ (d-spacing at 4.74 Å), 19.03±0.2° 2θ (4.66 Å), 24.24±0.2° 2θ (3.67 Å), 24.62±0.2° 2θ (3.61 Å) and 26.26±0.2° 2θ (3.39 Å). It may be further characterized by X-ray diffraction peaks at 16.78±0.2° 2θ (5.28 Å), 21.28±0.2° 2θ (4.17 Å), 23.77±0.2° 2θ (3.73 Å), 23.87±0.2° 2θ (3.72 Å) and 25.79±0.2° 2θ (3.45 Å). Crystalline sorafenib hydrobromide of Formula IV may also be characterized by a DSC thermogram having endotherm at about 262.27° C. Crystalline sorafenib hydrobromide of Formula IV may also be characterized by XRD spectrum, DSC thermogram, TGA and IR spectrum as depicted in FIGS. 5, 6, 7 and 8, respectively.

Crystalline sorafenib methane sulphonate of Formula V may be characterized by peaks in the powder X-ray diffraction pattern at about 16.37±0.2° 2θ (5.41 Å), 17.01±0.2° 2θ (5.20 Å), 21.41±0.2° 2θ (4.14 Å), 24.13±0.2° 2θ (3.68 Å) and 24.80±0.2° 2θ (3.58 Å). It may be further characterized by X-ray diffraction peaks at 8.18±0.2° 2θ (10.80 Å), 15.12±0.2° 2θ (5.85 Å), 17.01±0.2° 2θ (5.20 Å), 19.34±0.2° 2θ (4.58 Å) and 20.09±0.2° 2θ (4.41 Å). Crystalline sorafenib methane sulphonate of Formula V may also be characterized by DSC thermogram having endotherm at about 205.07° C. Crystalline sorafenib methane sulphonate of Formula V may also be characterized by XRD spectrum, DSC thermogram, TGA and IR spectrum as depicted in FIGS. 9, 10, 11 and 12, respectively.

Amorphous sorafenib sulphate of Formula VI may be characterized by XRD spectrum, DSC thermogram, TGA and IR spectrum as depicted in FIGS. 13, 14, 15 and 16, respectively.

Sorafenib free base to be used for the preparation of acid addition salts of the present invention may be obtained by any of the methods known in the literature such as those described in PCT publications WO 00/42012, WO 2006/034796, WO 2006/034797, WO 2009/034308, WO 2009/054004, WO 2009/106825 and WO 2009/092070, which are incorporated herein by reference.

In general, sorafenib freebase may be prepared by the reaction of 4-(2-(N-methylcarbamoyl)-4-pyridyloxy) aniline with 4-chloro-3-(trifluoromethyl) phenyl isocyanate. The starting sorafenib freebase may be obtained as a solution directly from a reaction in which sorafenib is formed and used as such without isolation.

The sorafenib acid addition salts may be prepared by contacting sorafenib free base with an acid of Formula HX.

The term "acid addition salt" as used in this application means a salt of an acid selected from the group containing hydrochloric acid, hydrobromic acid, sulfuric acid, phosphoric acid, methanesulphonic acid, trifluoromethanesulfonic acid, benzenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid and mandelic acid.

The term "contacting" may include dissolving, slurrying, stirring or a combination thereof.

The reaction of sorafenib free base with an acid of Formula HX may be carried out by directly contacting sorafenib free base with the acid of Formula HX. The reaction may also be carried out in the presence of a suitable solvent. A solution of the acid of Formula HX in a suitable solvent may also be used.

The suitable solvent may be selected from the group comprising of water, polar organic solvents, dipolar aprotic organic solvents and mixtures thereof.

Polar organic solvents may be selected from the group consisting of organic solvents containing 1-5 carbon atoms and at least one hydroxyl group, cyclic ethers, alkyl acetates and mixtures thereof. Examples of organic solvents containing 1-5 carbon atoms and at least one hydroxyl group are methanol, ethanol, n-propanol, isopropanol, n-butanol, sec-butanol, isobutanol, n-pentanol, glycerol or ethylene glycol. Examples of cyclic ethers are tetrahydrofuran or 1,4-dioxane. Examples of alkyl acetates are methyl acetate, ethyl acetate, propyl acetate or butyl acetate.

Dipolar aprotic organic solvents may be selected from the group consisting of ketones, amides, nitriles, sulphoxides or mixtures thereof. Examples of ketones are acetone, methyl ethyl ketone or methyl isobutyl ketone. Examples of amides are N,N-dimethylformamide or N,N-dimethylacetamide. Examples of nitriles are acetonitrile or propionitrile. Examples of sulphoxides are dimethyl sulfoxide or diethyl sulphoxide.

In the preferred embodiments of the present invention, the reaction of sorafenib free base with an acid of Formula HX may be carried out in polar organic solvents selected from organic solvents containing 1-5 carbon atoms and at least one hydroxyl group, such as methanol, ethanol, n-propanol, isopropanol, n-butanol, sec-butanol, isobutanol, n-pentanol, glycerol or ethylene glycol.

In some other preferred embodiments of the present invention, the reaction of sorafenib free base with an acid of Formula HX may be carried out by directly contacting sorafenib free base with acid of Formula HX.

The reaction of sorafenib free base with an acid of Formula HX may be carried out at a temperature of about −5° C. to about 100° C.

In one embodiment, the reaction of sorafenib free base with an acid of Formula HX may be carried out at about 0° C. In another embodiment, the reaction of sorafenib free base with an acid of Formula HX may be carried out at about 25° C. to about 35° C. In yet another embodiment, the reaction of sorafenib free base with an acid of Formula HX may be carried out at about 50° C. to about 80° C.

The reaction of sorafenib free base with an acid of Formula HX may be carried out for a period of about 10 minutes to about 8 hours, preferably for about 15 minutes to about 6 hours.

An anti-solvent may be added to the reaction mixture. The anti-solvent may be selected from the group consisting of hydrocarbons, ethers, chlorinated hydrocarbons and mixtures thereof. Examples of hydrocarbons are hexane, cyclohexane, benzene, toluene, heptane or octane. Examples of ethers are diethyl ether, methyl tert-butyl ether or diisopropyl ether. Examples of chlorinated hydrocarbons are chloroform, dichloromethane or 1,2-dichloroethane, water.

In the preferred embodiments of the present invention, the anti-solvent may be selected from the group comprising of ethers such as diethyl ether, methyl tert-butyl ether or diisopropyl ether.

The reaction mixture may be stirred for about 30 minutes to about 2 hours, preferably for about 1 hour.

Water may be removed from the reaction mixture by forming an azeotrope with a suitable solvent. The suitable solvent may be selected from hydrocarbons and mixtures thereof with chlorinated hydrocarbons, dipolar aprotic solvents and water. In the preferred embodiment of the present invention, water may be removed from the reaction mixture by forming an azeotrope with a hydrocarbon such as hexane, cyclohexane, benzene, toluene, heptane or octane.

Isolation may be accomplished by concentration, precipitation, cooling, filtration or centrifugation, or a combination thereof, followed by drying.

The acid addition salts of Formula VII may be further purified by trituration or crystallization in a suitable solvent. The suitable solvent may be selected from hydrocarbons, alkyl acetates or mixtures thereof.

In a preferred embodiment of the present invention, the acid addition salts of Formula VII may be purified by trituration in a hydrocarbon solvent such as hexane, cyclohexane, benzene, toluene, heptane or octane.

The processes of the present invention provide acid addition salts of sorafenib of Formula VII having high purity.

Solvates and hydrates of acid addition salts of Formula VII are also included within the scope of the present invention.

The acid addition salts of Formula VII may be conventionally formulated into tablets, capsules, suspensions, dispersions, injectables and other pharmaceutical forms. Any suitable route of administration may be employed for example peroral or parental.

The acid addition salts of sorafenib may be further used for preparation of sorafenib of Formula I of high purity by contacting with a base. The base may be selected from group comprising of hydroxides, carbonates and bicarbonates of alkali and alkaline earth metals, ammonia, alkyl amines, hydrazine and the like. Examples of hydroxides, carbonates and bicarbonates of alkali and alkaline earth metals may include lithium hydroxide, sodium hydroxide, potassium hydroxide, sodium carbonate, potassium carbonate, sodium bicarbonate or potassium bicarbonate. Examples of alkyl amines may include diethyl amine, triethyl amine or methyl diethyl amine.

The processes of the present invention provide sorafenib free base of high purity.

In the foregoing section, embodiments are described by way of examples to illustrate the process of invention. However, this is not intended in any way to limit the scope of the present invention. Several variants of the examples would be evident to persons ordinarily skilled in the art which are within the scope of the present invention.

Methods
XRD
Instrument: Panalytical
Mode: Expert PRO
Detector: Xcelerator
ScanRange: 3-40
Step size: 0.02
Range: 3-40° 2θ
DSC Mettler Toledo (DSC 821e)
TGA TA instruments (Q 500)

EXAMPLES

Example 1

Preparation of Sorafenib Hydrochloride

Methanol (5 mL) was added to a reaction vessel containing sorafenib free base (1.0 g) and the reaction mixture was stirred for about 5 minutes. Methanolic HCl (5 mL) was added gradually to the above reaction mixture at 0° C. The reaction mixture was stirred for about 1 hour. Diisopropyl ether (10 mL) was added. The reaction mixture was stirred for about 1 hour. The solid was filtered and dried under reduced pressure at about 50° C. for about 3 hours to obtain sorafenib hydrochloride.

Yield: 74.7%

Example 2

Preparation of Sorafenib Hydrochloride

Methanol (35 mL) was added to a reaction vessel containing sorafenib free base (7.0 g) and the reaction mixture was stirred for about 5 minutes. Methanolic HCl (35 mL) was added drop wise to the above reaction mixture at 0° C. The reaction mixture was stirred for about 1 hour. Diisopropyl ether (70 mL) was added. The reaction mixture was stirred for about 1 hour. The solid was filtered and dried under reduced pressure at about 50° C. for about 3 hours. The solid was triturated with toluene (20 mL) and reaction mixture was concentrated. The solid was washed with toluene (2×20 mL), dried under reduced pressure at about 30° C. for about 24 hours to obtain sorafenib hydrochloride.

Yield: 55%

Example 3

Preparation of Sorafenib Hydrobromide

Aqueous hydrogen bromide (15 mL) was added to a reaction vessel containing sorafenib free base (3.0 g) and the reaction mixture was stirred for about 5 minutes. Temperature was raised to about 70° C. The reaction mixture was stirred for about 2 hours. Solid precipitated out. The reaction mixture was concentrated and purified by adding toluene (3×15 mL) and concentrated to obtain a solid. Ethanol (2 mL) was added. The reaction mixture was stirred for about 5 minutes followed by addition of diisopropyl ether (5 mL). The solid was filtered and dried at about 50° C. for about 12 hours to obtain sorafenib hydrobromide.

Yield: 73.8%

Example 4

Preparation of Sorafenib Methane Sulphonate

Ethanol (10 mL) was added to a reaction vessel containing sorafenib free base (4 g). The reaction mixture was stirred for about 5 minutes. Methane sulphonic acid (0.55 mL) was added drop wise. The reaction mixture was stirred for about 4-5 hours. The solid was filtered, washed with ethanol (2×10 mL) and dried under reduced pressure at about 50° C. for about 12 hours to obtain sorafenib methane sulphonate.

Yield: 66%

Example 5

Preparation of Sorafenib Sulphate

Ethanol (25 mL) was added to a reaction vessel containing sorafenib free base (5 g). The reaction mixture was stirred for about 5 minutes. Temperature was raised to about 60° C. The reaction mixture was stirred for about 30 minutes. Sulphuric acid solution (sulphuric acid: ethanol: water: 0.57 mL: 6 mL: 19 mL) was added drop wise. The reaction mixture was cooled to room temperature and stirred for about 12 hours. The reaction mixture was concentrated. The solid was filtered and dried under reduced pressure at about 50° C. for about 12 hours to obtain sorafenib sulphate.

Yield: 89%

We claim:

1. Crystalline sorafenib hydrochloride of Formula III

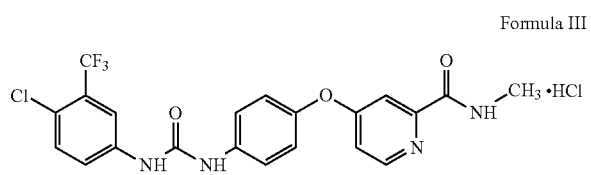 [SMILES: CNC(=O)c1cc(Oc2ccc(NC(=O)Nc3ccc(Cl)c(C(F)(F)F)c3)cc2)ccn1 ; Cl]

Formula III characterized by X-ray diffraction peaks having d-spacing values at about 3.69, 3.63, 3.42, 3.39 and 3.05 Å.

2. Crystalline sorafenib hydrochloride of claim 1 further characterized by X-ray diffraction peaks having d-spacing values at about 6.40, 4.22, 4.06 and 3.60 Å.

3. Crystalline sorafenib hydrochloride of claim 1 characterized by DSC thermogram having endotherms at about 68[0.33]° C., 115[0.21]° C. and 152[0.74]° C.

4. Crystalline sorafenib hydrochloride of claim 1 characterized by X-ray diffraction spectrum, DSC thermogram, TGA and IR spectrum as depicted in FIGS. 1, 2, 3 and 4, respectively.

5. A pharmaceutical composition comprising crystalline sorafenib hydrochloride of Formula III.

* * * * *

UNITED STATES PATENT AND TRADEMARK OFFICE
CERTIFICATE OF CORRECTION

PATENT NO. : 8,604,208 B2
APPLICATION NO. : 13/497861
DATED : December 10, 2013
INVENTOR(S) : Jagdev Singh Jaryal et al.

It is certified that error appears in the above-identified patent and that said Letters Patent is hereby corrected as shown below:

In the Claims

COLUMN 10, Claim 3, lines 18-20:

"Crystalline sorafenib hydrochloride of claim 1 characterized by DSC thermogram having endotherms at about 68[0.33]°C, 115[0.21]°C and 152[0.74]°C." should read -- Crystalline sorafenib hydrochloride of claim 1 characterized by DSC thermogram having endotherms at about 68°C, 115°C and 152°C. --

Signed and Sealed this
Third Day of February, 2015

Michelle K. Lee
*Deputy Director of the United States Patent and Trademark Office*